(12) United States Patent
Burke et al.

(10) Patent No.: US 6,475,227 B2
(45) Date of Patent: Nov. 5, 2002

(54) VASO-OCCLUSION APPARATUS HAVING A MECHANICALLY EXPANDABLE DETACHMENT JOINT AND A METHOD FOR USING THE APPARATUS

(75) Inventors: Thomas H. Burke, Dearborn, MI (US); Kim Nguyen, San Jose, CA (US); Henry Bourang, Turlock, CA (US); Uriel Hiram Chee, San Carlos, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/184,567

(22) Filed: Nov. 2, 1998

(65) Prior Publication Data

US 2002/0058954 A1 May 16, 2002

(Under 37 CFR 1.47)

Related U.S. Application Data

(63) Continuation of application No. 08/998,121, filed on Dec. 24, 1997, now abandoned.

(51) Int. Cl.[7] .............................................. A61M 29/00
(52) U.S. Cl. ........................................ 606/198; 606/108
(58) Field of Search ................................. 606/158, 151, 606/108, 200, 191, 194, 198; 604/98.02, 93.01, 95.04, 96.01; 623/1.11

(56) References Cited

U.S. PATENT DOCUMENTS

| 3,834,394 A | 9/1974 | Hunter et al. |
|---|---|---|
| 3,868,956 A | 3/1975 | Alfidi et al. |
| 4,650,466 A | * 3/1987 | Luther ..................... 604/95.04 |
| 5,109,867 A | 5/1992 | Twyford, Jr. |
| 5,122,136 A | 6/1992 | Guglielmi et al. |

(List continued on next page.)

FOREIGN PATENT DOCUMENTS

| FR | 2 712 797 | 2/1995 |
| WO | WO 97/48351 | 12/1997 |
| WO | WO 98/02100 | 1/1998 |
| WO | WO 98/04198 | 2/1998 |
| WO | WO 98/04315 | 2/1998 |

OTHER PUBLICATIONS

Anderson et al., "Transcatheter Intravascular Coil Occlusion of Experimental Arteriovenous Fistulas" *AJR Am J Roentgenol.* 129(5):795–8 (Nov. 1977).
BALT Extrusion (France), "Mechanical Detachment System for SPIRALE," Sales Brochure (1993).

Primary Examiner—Kennedy Schaetzle
Assistant Examiner—Kristen Droesch
(74) Attorney, Agent, or Firm—Lyon & Lyon LLP

(57) ABSTRACT

A flexible engaging delivery device (10) for delivery of a vaso-occlusion flexible engaging structure (24) to a vascular target site via a catheter (50) is disclosed comprising a catheter (50) having a lumen (52) and an introducer (48) disposed within the catheter (52). The introducer (48) comprises an outer sleeve (49), a shaft (12) and a wire (16) that is slidably movable within the shaft (12). A wire tip (22) is permanently connected to the wire (16), wherein the wire tip (22) is adapted to contact a matted portion (20) of the vaso-occlusion flexible engaging structure (24) and is used to deliver said flexible engaging structure from said flexible engaging device (10) to a vaso-occlusion target site.

10 Claims, 3 Drawing Sheets

U.S. PATENT DOCUMENTS

| | | |
|---|---|---|
| 5,217,484 A | 6/1993 | Marks |
| 5,234,437 A | 8/1993 | Sepetka |
| 5,250,071 A | 10/1993 | Palermo |
| 5,261,916 A | 11/1993 | Engelson |
| 5,263,964 A | 11/1993 | Purdy |
| 5,304,195 A | 4/1994 | Twyford, Jr. et al. |
| 5,312,415 A | 5/1994 | Palermo |
| 5,350,397 A | 9/1994 | Palermo et al. |
| 5,354,295 A | 10/1994 | Guglielmi et al. |
| 5,423,829 A | 6/1995 | Pham et al. |
| 5,445,646 A | 8/1995 | Euteneuer et al. |
| 5,476,472 A * | 12/1995 | Dormandy, Jr. et al. .... 606/151 |
| 5,522,836 A | 6/1996 | Palermo |
| 5,562,698 A | 10/1996 | Parker |
| 5,578,074 A | 11/1996 | Mirigian |
| 5,624,449 A | 4/1997 | Pham et al. |
| 5,632,749 A * | 5/1997 | Goode et al. ................ 606/108 |
| 5,653,684 A * | 8/1997 | Laptewicz et al. ............ 604/22 |
| 5,733,294 A | 3/1998 | Forber et al. |
| 5,743,905 A | 4/1998 | Eder et al. |
| 5,800,454 A | 9/1998 | Jacobsen et al. |
| 5,814,062 A * | 9/1998 | Sepetka et al. ............. 606/198 |
| 5,855,578 A | 1/1999 | Guglielmi et al. |
| 5,891,128 A | 4/1999 | Gia et al. |
| 5,891,130 A | 4/1999 | Palermo et al. |
| 5,895,385 A | 4/1999 | Guglielmi et al. |
| 5,895,391 A | 4/1999 | Farnholtz |
| 5,911,717 A | 6/1999 | Jacobsen et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,060 A | 7/1999 | Forber |
| 5,925,062 A | 7/1999 | Purdy |
| 5,928,226 A | 7/1999 | Guglielmi et al. |
| 5,944,714 A | 8/1999 | Guglielmi et al. |
| 5,989,242 A | 11/1999 | Saadat et al. |
| 6,238,412 B1 * | 5/2001 | Dubrul et al. .............. 606/200 |

* cited by examiner

VASO-OCCLUSION APPARATUS HAVING A MECHANICALLY EXPANDABLE DETACHMENT JOINT AND A METHOD FOR USING THE APPARATUS

CROSS-REFERENCE TO RELATED APPLICATIONS

This application is a continuation of U.S. application Ser. No. 08/998,121, filed Dec. 24, 1997, now abandoned.

FIELD OF THE INVENTION

A flexible engaging delivery device for delivery of a vaso-occlusion flexible engaging structure to a vascular target site via a catheter is disclosed comprising a catheter having a lumen and an introducer disposed within the catheter. The introducer comprises an outer sleeve, a shaft, and a wire that is slidably movable within the shaft. A wire tip is permanently connected to the wire, wherein the wire tip is adapted to contact a matted portion of the vaso-occlusion flexible engaging structure and is used to deliver said flexible engaging structure from said flexible engaging device to a vaso-occlusion target site.

BACKGROUND OF THE INVENTION

In a variety of medical procedures, a physician may need to occlude vessels in order to contain bleeding or reduce the risk of hemorrhaging.

There are a variety of devices that have been developed to occlude blood vessels. One of these employs a catheter to deliver one or more vaso-occlusion coils to a vascular target site. The vaso-occlusion coils are typically platinum or other surgical-metal coils that are delivered via a vascular catheter. Typically, the coil is placed in a linear condition in the catheter, and is pushed from the end of the catheter by a pusher wire. As the coil exits the delivery device it assumes a relaxed, convoluted shape at the vascular site.

The coil may be deployed simply by ejecting it from the distal end of the catheter. However, this technique may be unsatisfactory where it is desired to better position the coil in the vessel once it has been ejected from the catheter and has assumed its convoluted shape. To overcome this problem, various release mechanisms have been proposed to allow for positive release of the coil from the end of a pusher wire once the coil is properly positioned at the vascular site. Expandable jaw clamps and electrolytically erodible joints are examples of such mechanisms.

It would be advantageous to provide a coil delivery device and catheter assembly which provides the combined advantages of (i) a coil release mechanism that allows for simple coil loading and release, (ii) positive release once the coil is properly positioned at the target site, (iii) multiple reloading steps, and (iv) operable with coils having a variety of coil diameters.

SUMMARY OF THE INVENTION

The invention includes, in one embodiment, a coil-delivery device for delivery to a vascular target site via an inner-lumen catheter, an elongate, flexible vaso-occlusion coil having an end-region inner lumen. The device includes an elongate sleeve, perhaps a catheter, having proximal and distal ends and an inner lumen extending therebetween, and a wire slidably movable within said sleeve. The wire has a distal end region extending beyond the distal end of the sleeve, and a proximal end region that can be manipulated to move the wire between extended and retracted positions with respect to the sleeve's distal end. A flexible engaging structure in the device extends between the distal ends of the sleeve and the wire, such that movement of the wire between its extended and retracted positions is effective to move the flexible engaging structure between extended and radially expanded conditions, respectively, in which the engaging structure is adapted to be received within and compressionally engage the lumen end region of the coil, respectively.

The engaging structure in the device may be braided, generally in the shape of a sock. The structure may be dimensioned, with such in its extended position, to be received in the inner lumen of a coil having an outer diameter as small as 15 mils, and with such in its expanded condition, to compressionally engage the lumen end region of a coil having an outer diameter as great as 35 mils.

In another aspect, the invention includes a coil-delivery assembly for delivery of at least one, and preferably a plurality of vaso-occlusion coils to a vascular target site. The assembly includes (a) a catheter having proximal and distal ends, and an inner lumen extending therebetween, (b) an introducer for holding a vaso-occlusion coil in a substantially linear condition, and (c) a coildelivery device of the type described above. The introducer may have an end region adapted to be mated with the proximal end of said catheter, for transferring a coil from the introducer into the catheter. The assembly allows a coil to be frictionally and releasably engaged by the wire, with the coil held in the introducer, transferred from the introducer into and through the catheter, and released from the wire after being advanced across the catheter's distal end.

Also disclosed is a method for releasably engaging a vaso-occlusion coil of the type having an end-region inner lumen. The method involves immobilizing the coil in a substantially linear condition in a tube having an open access end, inserting into the tube, a coil-delivery device of the type described above, and moving the wire in the device to its retracted position to compressionally engage the engaging member with the inner lumen of the coil.

These and other objects and features of the invention will become more fully apparent when the following detailed description of the invention is read in conjunction with the accompanying drawings.

BREIF DESCRIPTION OF THE DRAWINGS

DETAILED DESCRIPTION OF THE INVENTION

Figure 1:
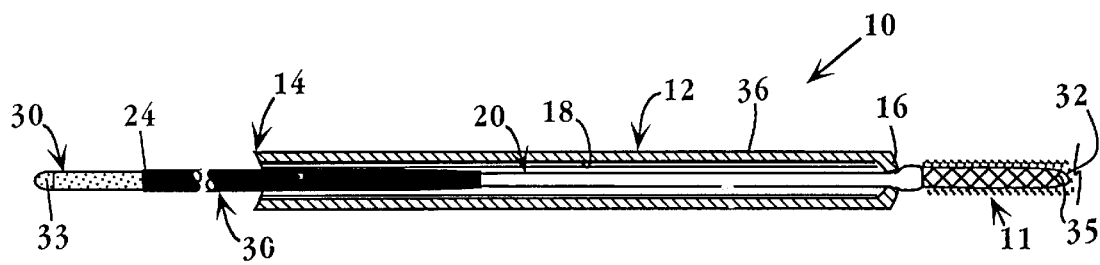
FIG. 1 is a fragmentary cross-sectional view of a catheter and coil delivery ice in a coil delivery assembly constructed according to the invention.
Figure 2A:
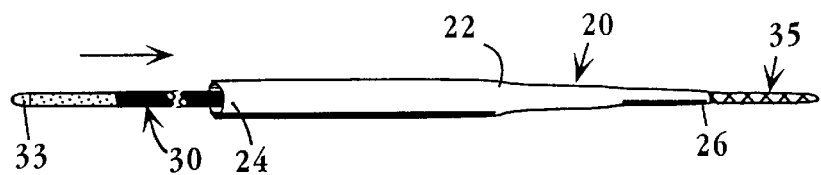
FIGS. 2A and 2B show, respectively, a fragmentary side view and a sidetional view of a coil-delivery device constructed in accordance with the vention, with its distal end region shown in an extended state.
Figure 2B:
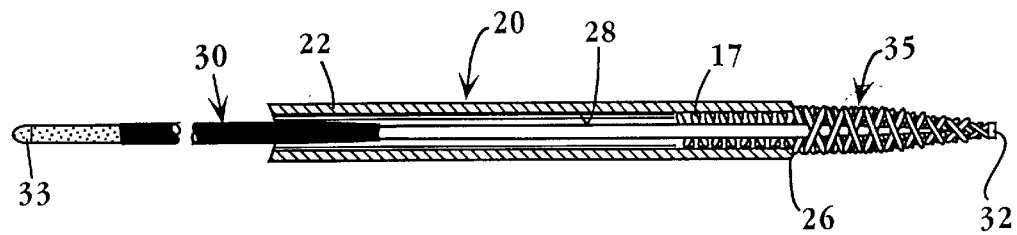

FIG. 1 illustrates components of one embodiment of a coil-delivery assembly 10 for delivering one or more coils, such as coil 11, to a vascular target site. The assembly includes a catheter 12 having proximal and distal ends 14, 16, respectively, and an inner lumen 18 extending therebetween.

As seen particularly in FIGS. 2A and 2B and 3A and 3B, a coil-delivery device 20 in the assembly includes an elongate sleeve 22 having proximal and distal ends 24, 26, respectively, and an inner lumen 28 extending therebetween. A wire 30 in the device is slidably movable within the sleeve. The wire has a distal end 32 extending beyond the distal end of the sleeve, and a proximal end region 33 that can be manipulated to move the wire between extended and retracted positions with respect to the sleeve's distal end.

Figure 3A:
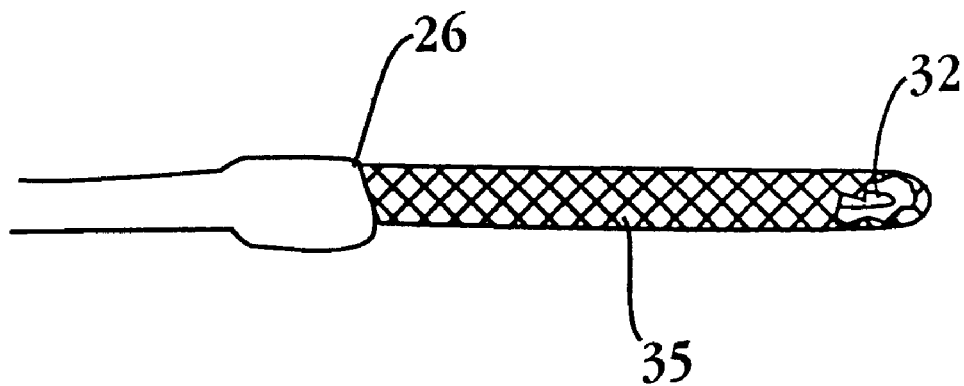
FIGS. 3A and 3B show the distal end of a coil-delivery device of FIG. 2A and 2B with the distal end region in an expanded state.
Figure 3B:
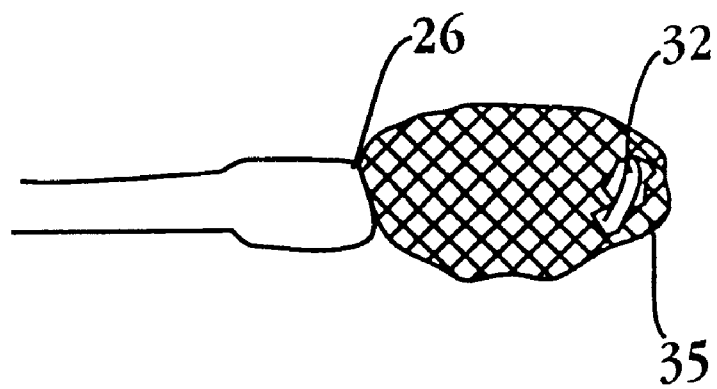

A flexible engaging structure 35 in the delivery device extends between the distal ends of the sleeve and the wire, such that movement of the wire between its extended and retracted positions is effective to move the flexible engaging structure between extended and radially expanded conditions, indicated in FIGS. 3A and 3B, respectively.

Also included in the assembly is an introducer (shown at 34 in FIGS. 4 and 5) for use in introducing a coil, such as coil 11, carried on device 20 into the catheter, in a manner to be described.

Considering now details of the assembly, catheter 12 may be a conventional single-lumen catheter for use in accessing a vascular target site, e.g., along tortuous-path, narrow vessels. The catheter is formed of a flexible tubing 36, typically about 100–300 cm in length, which may have a reduced thickness and/or stiffness on progressing from the proximal to distal ends, to allow improved target site accessing in deep tissue. The inner diameter of the catheter, i.e., lumen diameter, may vary in size according to the size of the coil to be delivered. Typical catheter cross-sectional dimensions are between about 10–100 mils inner diameter, and between about 5–20 mils tubing wall thickness. The catheter's inner wall may have a lubricous coating to improve the easy of movement of device 20 and a coil carried therewith, through the catheter.

Wire 30 in device 20 may be, for example, a flexible torqueable guide wire having a total length between about 100–300 cm and a maximum diameter of the wire between about 8–40 mils (thousandths of an inch). The body portion of the wire may have a substantially constant diameter along its length, or may contain regions of taper. In one embodiment, the wire has a tapered distal portion of about 5–50 cm in length, and preferably about 15–20 cm in length, with the body portion making up the remainder of the length of the wire. The taper is preferably such as to reduce the diameter of the wire from about 8–40 mils at the proximal end to a minimum diameter of typically 1–5 mils at the distal wire end. Stainless steel wire of suitable for making device 20 type is commercially available, e.g., from Wytech and National Standard.

Sleeve 22 in device 20 is formed of a flexible tubing whose inner diameter allows axial movement of wire 30 within the sleeve between the wire's extended and retracted positions. The tubing may have a reduced diameter and/or stiffness on progressing from the proximal to the distal end. The tubing has a preferred length between about 100–300 cm and a maximum diameter of about 20–50 mils. The outer diameter of the sleeve is dimensioned to allow the wire device, including the sleeve, to be advanced axially through the catheter, to place the distal end region of the device beyond the distal end of the catheter, for coil placement and release at the target site. The outer diameter at the distal end of the sleeve is greater than the inner lumen diameter of a coil, such as coil 11, to be delivered by the device.

Engaging structure 35 is preferably a braided sock formed by braided metal filaments or the like. Such braided sleeves or socks are commercially available in a variety of sleeve diameters, for example, 5–20 mils, from Viamed Corp (South Easton, Mass.), or may be braided using braiders such as supplied by Steeger (Spartanburg, S.C.).

The sock is preferably about 1–3 cm in length, and has a "relaxed" diameter similar to that of the outer diameter of the sleeve's distal end. As will be seen, the sock can be stretched, in its extended condition, to a diameter smaller than its "relaxed" diameter, and in particular, smaller than the inner lumen diameter of a coil to be releasably engaged by the device, e.g., 3–8 mils. At the same time, the sock diameter can be expanded radially, by reducing its length, to a maximum diameter of up to 30–50 mils or more.

The braided sock is attached at its proximal end to the distal end of sleeve 22 by conventional methods. For example, the proximal end of the sock may be placed over the distal end of the sleeve, and the interface covered with a layer of a suitable resin capable of bonding to the sleeve.

The distal end of the sock is attached to the distal end of wire 30, such that movement of the wire between its extended and retracted positions is effective to move the sock between its extended and radially expanded conditions, respectively. The attachment of the wire to the distal end of the sock may be, for example, by a solder joint or other suitable bonding agent.

The coil-delivery device just disclosed, as embodied in device 20, also forms one aspect of the invention.

Figure 4:
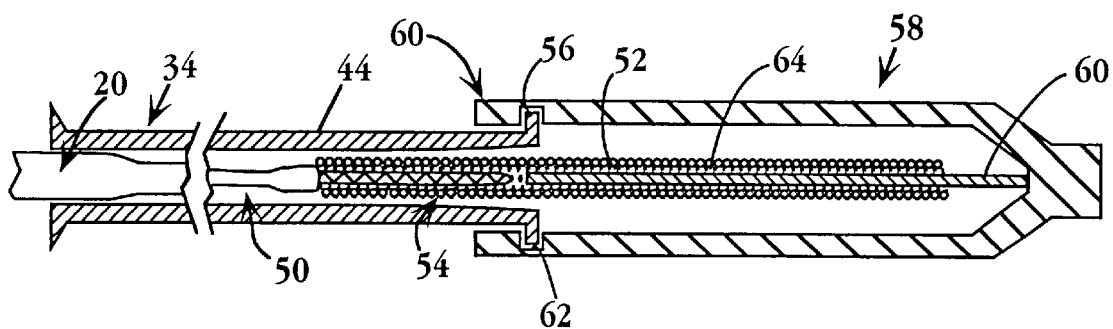
FIG. 4 is a partial cross sectional view of a delivery device and introducer used in transferring a coil from a supply tube to the introducer.

As indicated above, assembly 10 further includes an introducer for use in transferring a coil from the introducer into the catheter in the assembly. FIG. 4 illustrates such an introducer, indicated here at 34. The introducer defines an inner cylindrical cavity 50 which is open at both ends. The introducer is dimensioned to receive a vaso-occlusion coil, such as coil 52, within the cavity. The introducer's distal end, indicated here at 54, has a flange 56 for releasably engaging annular groove 62 in the open end of a coil-supply tube 58.

In a typical embodiment, where multiple coils are to be delivered, each coil is supplied in a tube, such as tube 58, which is closed at one end, and open at its opposite end, here indicated at 60. The open end has an annular groove 62 for receiving flange 56, to engage the introducer by snap-fit, and anchor the introducer releasably to the coil-supply tube during a coil-transfer operation.

Figure 5:
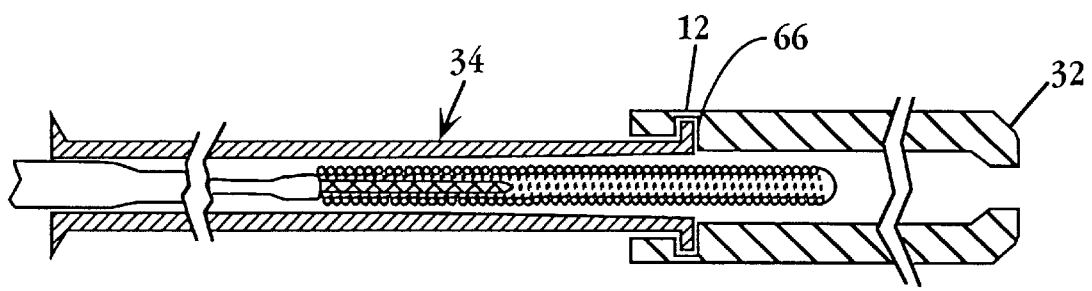
FIG. 5 is a partial cross sectional view illustrating transfer of a vaso-occlusion coil from an introducer into a catheter.

A variety of coils, such as coil 52, may be suitable. One example of a coil 52 for delivery by the present invention is "flower coil" available from Target Therapeutics (Fremont, Calif.). This coil can be easily constrained to a linear condition, but will "fold" into a convoluted vaso-occlusion condition when released from its linear constraints. Typical coil lengths are between about 1–50 cm. Typical outer coil diameters are between about 15–35 mils. As seen in FIG. 5, the coil includes an inner lumen extending the length of the coil. This lumen has typical diameters between and 5 and 25 mils.

Operation of the assembly will now be described. Initially, catheter 12 in the assembly is directed to a selected vascular target site, e.g., using a conventional guide wire to guide the catheter through a vessel path. The guide wire is then removed, leaving the catheter in place to serve as a conduit for delivering coils from the proximal, accessible catheter end to the target site adjacent the catheter's distal end.

With respect particularly to FIGS. 4 and 5, to supply the first coil to the target site, a vaso-occlusion coil having a selected length and diameter is transferred from a supply tube, via the introducer, into the catheter. This is done by attaching the distal introducer 34 end, by snap-fit engagement, to a coil-supply tube, such as tube 58. Device 20 is then inserted through the introducer 34 and into the coil-supply tube 58, with the braided sock in its extended, small-diameter condition, allowing the sock to be received in the inner lumen of the open end region of the coil. That is, wire 30 (see FIG. 2A) in the device 20 is moved to its extended condition and held in this condition as the wire device 20 as a unit is advanced axially into the introducer 34. The sock is inserted substantially all the way into the coil lumen, this advancement being arrested when the coil end abuts the distal end of sleeve 22 (FIG. 2A) in the device. The wire 30 in the device 20 is now moved toward its retracted position, causing the sock to expand radially and to compressionally engage the lumen of coil 64. With the wire held in its retracted position, the coil 64 may now be removed from its supply tube 58 and drawn completely into the introducer cavity 44 by retracting the device 20 into and substantially through the introducer 34.

As shown in FIG. 5, the introducer 34 is now disengaged from the supply tube and snap-fit engaged with catheter 12 which has an end groove 66 (similar to groove 62 in supply tube 58 in FIG. 4). The coil-delivery device assembly, as depicted in FIG. 5, may be advanced in the direction of the catheter's 12 distal end, ultimately until the attached coil is discharged from the distal end of the catheter, where the coil assumes its convoluted, vaso-occluding condition. The delivery device may be further manipulated at this stage, until the coil is optimally positioned at the target site. When this positioning is achieved, the wire (30 in FIG. 2A) in the device 20 is extended to extend the braided sock in its small-diameter condition, allowing the coil 64 to released from the delivery device 20 by retracting the braided sock, e.g., into the catheter.

The coil-delivery device 20 is then withdrawn from the catheter 12 and a new coil may be (i) transferred from its supply tube to the introducer, (ii) transferred from the introducer to catheter, and (iii) released from the wavy segment at a selected position at the target site, as described above. This reloading and new coil placement at the target site is repeated unto a desired number of coils have been placed at the site.

From the foregoing, it will be appreciated how various objects and features of the invention have been met. The delivery device allows a coil, e.g., supplied in a supply tube, to be releasably engaged by inserting the braided sock in the device into the supply tube until the sock is inserted into an end region of the coil's inner lumen, and retracting the device wire to produce a compressional engagement of the device with the coil. Once releasably attached to device, the coil can be positively manipulated into and through a catheter and released at a selected vascular site, simply by retracting the wire in the device. This allows for simple reloading and release of multiple coils during a coil vaso-occlusion procedure.

Further, the engagement structure in the device, e.g., a braided sock, is adapted to compressionally engage coils having a variety of different lumen sizes, and thus the physician can select a range of coil sizes to be placed without replacing any of the assembly components.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

It is claimed:

1. A coil-delivery device for delivery to a vascular target site via an inner-lumen catheter, an elongate, flexible vaso-occlusion coil having an end-region inner lumen, said device comprising:

an elongate sleeve having proximal and distal ends and an inner lumen extending therebetween, a wire slidably movable within said sleeve, said wire having a distal end region extending beyond the distal end of the sleeve, and a proximal end region that can be manipulated to move the wire between extended and retracted positions with respect to the sleeve's distal end, and a flexible engaging structure having a proximal end attached to the sleeve's distal end and a distal end attached to the wire distal to the sleeve's distal end, such that movement of the wire between its extended and retracted positions is effective to move the flexible engaging structure between extended and radially expanded conditions, respectively, in which the engaging structure is adapted to be received within and compressionally engage the lumen end region of the coil, respectively, wherein said elongate sleeve has an outer diameter at the distal end such that the elongate sleeve abuts an end of the coil when the engaging structure is received within the lumen end region of the coil.

2. The device of claim 1, wherein the flexible engaging structure is a braided sock.

3. A coil-delivery device for delivery to a vascular target site via an inner-lumen catheter, an elongate, flexible vaso-occlusion coil having an end-region inner lumen, said device comprising:

an elongate sleeve having proximal and distal ends and an inner lumen extending therebetween, a wire slidably movable within said sleeve, said wire having a distal end region extending beyond the distal end of the sleeve, and a proximal end region that can be manipulated to move the wire between extended and retracted positions with respect to the sleeve's distal end, and a flexible engaging structure having a proximal end attached to the sleeve's distal end and a distal end attached to the wire distal to the sleeve's distal end, such that movement of the wire between its extended and retracted positions is effective to move the flexible engaging structure between extended and radially expanded conditions, respectively, in which the engaging structure is adapted to be received within and compressionally engage the lumen end region of the coil, respectively, wherein said engaging structure, with such in its extended condition, is adapted to be received in the inner lumen of a coil having an outer diameter as small as 15 mils, and with such in its expanded condition, to compressionally engage the lumen end region of a coil having an outer diameter as great as 35 mils.

4. The device of claim 3, wherein the flexible engaging structure is a braided sock.

5. A coil-delivery assembly for delivery of a plurality of vaso-occlusion coils to a vascular target site, comprising:

(a) a catheter having proximal and distal ends, and an inner lumen extending therebetween, (b) an introducer for holding a vaso-occlusion coil in a substantially linear condition, said introducer having an end region adapted to be mated with the proximal end of said catheter, for transferring a coil from the introducer into the catheter, said coils each having an end-region inner lumen, and (c) a coil-delivery device for delivery of such a coil to a target site via the catheter, said device having (i) an elongate sleeve having proximal and distal ends and an inner lumen extending therebetween, (ii) a wire slidably movable within said sleeve, said wire having a distal end region extending beyond the distal end of the sleeve, and a proximal end region that can be manipulated to move the wire between extended and retracted positions with respect to the sleeve's distal end, and (iii) a flexible engaging structure having a proximal end attached to the sleeve's distal end and a distal end attached to the wire distal to the sleeve's distal end, such that movement of the wire between its extended and retracted positions is effective to move the flexible engaging structure between extended and radially expanded conditions, respectively, in which the engaging structure is adapted to be received within and compressionally engage the lumen end region of the coil, respectively.

whereby the coil may be frictionally and releasably engaged by the flexible engaging structure, with the coil held in the introducer, transferred from the introducer into and through the catheter, and released from the flexible engaging structure after being advanced across the catheter's distal end.

6. The assembly of claim 5, wherein the engaging structure is a braided sock.

7. The assembly of claim 5, wherein said engaging structure, with such in its extended condition, is adapted to be received in the inner lumen of a coil having an outer diameter as small as 15 mils, and with such in its expanded condition, to compressionally engage the lumen end region of a coil having an outer diameter as great as 35 mils.

8. The assembly of claim 7, wherein the flexible engaging structure is a braided sock.

9. A method for releasably engaging a vaso-occlusion coil of the type having an end-region inner lumen, comprising of:

immobilizing the coil in a substantially linear condition in a tube having an open access end, inserting into said tube, a coil-delivery device having (i) an elongate sleeve having proximal and distal ends and an inner lumen extending therebetween, (ii) a wire slidably movable within said sleeve, said wire having a distal end region extending beyond the distal end of the sleeve, and a proximal end region that can be manipulated to move the wire between extended and retracted positions with respect to the sleeve's distal end, and (iii) a flexible engaging structure having a proximal end attached to the sleeve's distal end and a distal end attached to the wire distal to the sleeve's distal end, such that movement of the wire between its extended and retracted positions is effective to,move the flexible engaging structure between extended and radially expanded conditions, respectively, in which the engaging structure is adapted to be received within and compressionally engage the lumen end region of the coil, respectively, and moving the wire to its retracted position to compressionally engage the engaging member with the inner lumen of the coil.

10. The method of claim 9, for use in engaging a vaso-occlusion wire having an outer diameter between 15 and 35 mils, wherein said engaging structure, with such in its extended condition, is adapted to be received in the inner lumen of a coil having an outer diameter as small as 15 mils, and with such in its expanded condition, to compressionally engage the lumen end region of a coil having an outer diameter as great as 35 mils.

* * * * *

UNITED STATES PATENT AND TRADEMARK OFFICE
CERTIFICATE OF CORRECTION

PATENT NO. : 6,475,227 B2
DATED : November 5, 2002
INVENTOR(S) : Thomas H. Burke et al.

It is certified that error appears in the above-identified patent and that said Letters Patent is hereby corrected as shown below:

Column 2,
Line 22, replace "coildelivery" with -- coil-delivery"
Line 44, replace "ice" with -- device --
Line 47, replace "sidetional" with -- side-sectional --
Line 48, replace "vention" with -- invention --

Column 7,
Line 1, replace "vaso- occlusion" with -- vaso-occlusion --

Column 8,
Line 19, replace "to,move" with -- to move --

Signed and Sealed this

Twenty-second Day of June, 2004

JON W. DUDAS
*Acting Director of the United States Patent and Trademark Office*